(12) United States Patent
Koarashi (10) Patent No.: US 11,446,048 B2
(45) Date of Patent: Sep. 20, 2022

(54) TUNNEL DEVICE

(71) Applicant: HI-LEX Corporation, Hyogo (JP)

(72) Inventor: Shinsaku Koarashi, Hyogo (JP)

(73) Assignee: HI-LEX Corporation, Hyogo (JP)

( * ) Notice: Subject to any disclaimer, the term of this patent is extended or adjusted under 35 U.S.C. 154(b) by 239 days.

(21) Appl. No.: 16/626,521

(22) PCT Filed: Jun. 29, 2018

(86) PCT No.: PCT/JP2018/024788
§ 371 (c)(1),
(2) Date: Dec. 25, 2019

(87) PCT Pub. No.: WO2019/004422
PCT Pub. Date: Jan. 3, 2019

(65) Prior Publication Data
US 2020/0281615 A1    Sep. 10, 2020

(30) Foreign Application Priority Data

Jun. 29, 2017  (JP) .............................. JP2017-127313

(51) Int. Cl.
*A61B 17/32* (2006.01)
*A61B 17/00* (2006.01)
*A61M 25/01* (2006.01)

(52) U.S. Cl.
CPC ...... *A61B 17/32* (2013.01); *A61B 2017/0042* (2013.01); *A61B 2017/00858* (2013.01);
(Continued)

(58) Field of Classification Search
CPC ............ A61B 17/32; A61B 2017/0042; A61B 2017/00858; A61B 2017/320056; A61M 25/0194
See application file for complete search history.

(56) References Cited

U.S. PATENT DOCUMENTS 3,999,551 A    12/1976  Spitz et al.
5,306,240 A    4/1994   Berry
(Continued)

FOREIGN PATENT DOCUMENTS

| CN | 102525601 | 7/2015 |
|---|---|---|
| JP | 2011-079497 | 4/2011 |
| WO | WO 2019/004422 | 1/2019 |

OTHER PUBLICATIONS

International Search Report and the Written Opinion sated Sep. 18, 2018 From the International Searching Authority Re. Application No. PCT/JP2018/024788 and Its Translation of Search Report Into English. (13 Pages).

(Continued)

*Primary Examiner* — Brooke Nicole Labranche (57) ABSTRACT

A tunnel device includes a base portion, a shaft to be connected to the base portion at one end of the shaft, and a tip portion to be connected to another end of shaft. The base portion is provided with a shaft connection portion to which the one end of shaft is connected. The shaft is provided with a shaft-side screw portion at the one end of the shaft. The shaft connection portion includes a shaft housing portion having an inner diameter substantially same as an outer diameter of the one end of the shaft, and a base-portion side screw portion provided on a further inner side relative to the shaft housing portion. The base portion and the shaft are fixed to each other by screwing between the shaft-side screw portion and the base-portion side screw portion.

3 Claims, 6 Drawing Sheets

(52) U.S. Cl.
CPC ............ *A61B 2017/320056* (2013.01); *A61M 25/0194* (2013.01)

(56) References Cited

U.S. PATENT DOCUMENTS

| | | |
|---|---|---|
| 2004/0171997 A1* | 9/2004 | Wilson ................ A61M 1/3659 604/284 |
| 2007/0173879 A1 | 7/2007 | Pandey |
| 2012/0083794 A1 | 4/2012 | Martin et al. |
| 2015/0133951 A1 | 5/2015 | Seifert et al. |
| 2016/0158529 A1* | 6/2016 | Thompson-Nauman .................... A61N 1/05 606/129 |

OTHER PUBLICATIONS

Examination Report Under Sections 12 & 13 of the Patents Act, 1970 and the Patents Rules, 2003 dated Aug. 28, 2021 From the Government of India. Intellectual Property India, Patents, Designs, Trade Marks, Geographical Indications, The Patent Office Re. Application No. 201917053449. (6 Pages).

* cited by examiner

TUNNEL DEVICE

TECHNICAL FIELD

The present invention relates to a tunnel device.

BACKGROUND ART

For the purpose of implanting an artificial blood vessel for peripheral vascular reconstruction or dialysis, tunnel devices each forming a subcutaneous tunnel and implanting an artificial blood vessel subcutaneously have been used. For example, a tunnel device including a handle to be held, a shaft to be connected to the handle, and a chip portion to be attached to a tip of the shaft is disclosed in Patent Literature (hereinafter, referred to as "PTL") 1.

The tunnel device of PTL 1 is configured such that the shaft is detachably connected with respect to the handle. The connection of the shaft with respect to the handle is made by screwing a female screw portion formed on an inner peripheral surface of an end portion of the shaft with an outer periphery of a male screw portion provided so as to protrude from one end of the handle.

CITATION LIST

Patent Literature

PTL 1
U.S. Pat. No. 5,306,240

SUMMARY OF INVENTION

Technical Problem

However, when the tunnel device is conducted subcutaneously by operation for forming a subcutaneous tunnel, for example, a tip of the tunnel device is pushed by a physical force and moved forward subcutaneously, and thus, the tunnel device forms a passage for the shaft as a subcutaneous tunnel. When a subcutaneous tunnel is formed by such a tunnel device, the tunnel device touches a body fluid, and/or subcutaneous tissue scrapped off by friction with the tunnel device adheres to the tunnel device in some cases. In a case where a body fluid and/or subcutaneous tissue attaches to the tunnel device, the body fluid and/or subcutaneous tissue enters between the shaft and the handle in some cases. In the tunnel device described in PTL 1, a structure is adopted in which the tunnel device includes a shaft and a handle serving as a base portion to be connected to the shaft, and a female screw portion formed on an inner peripheral surface of an end portion of the shaft is screwed with an outer periphery of a male screw portion provided so as to protrude from one end of the handle. For this reason, the body fluid and/or a cell that has entered from a gap between the shaft and the handle during operation enters between the male screw portion and the female screw portion in some cases. Although tunnel devices are supposed to be disassembled and washed for each use, it is difficult to wash a groove portion of the female screw portion and/or male screw portion. More specifically, adhesion of a body fluid and/or the like to a place where cleaning is difficult, such as the female screw portion and/or male screw portion, results in a hygienic problem.

An object of the present invention is thus to provide a tunnel device which is safe and good in a hygienic aspect, such as cleaning.

Solution to Problem

A tunnel device of the present invention includes: a base portion; a shaft to be connected to the base portion at one end of the shaft; and a tip portion to be connected to another end of the shaft, in which the base portion is provided with a shaft connection portion to which the one end of the shaft is connected, and the shaft is provided with a shaft-side screw portion at the one end of the shaft, in which the shaft connection portion includes: a shaft housing portion having an inner diameter substantially same as an outer diameter of the one end of the shaft; and a base-portion-side screw portion provided on a further inner side relative to the shaft housing portion, in which the base portion and the shaft are fixed to each other by screwing between the shaft-side screw portion and the base-portion-side screw portion.

Advantageous Effects of Invention

According to the tunnel device of the present invention, a tunnel device which is good in a hygienic aspect, such as cleaning, can be used in a hygienically safe manner.

DESCRIPTION OF EMBODIMENTS

Hereinafter, a tunnel device according to one embodiment of the present invention will be described with reference to the accompanying drawings. Note that, the embodiment indicated hereinafter is just an example, and the tunnel device of the present invention is not limited to the following embodiment.

Figure 1:
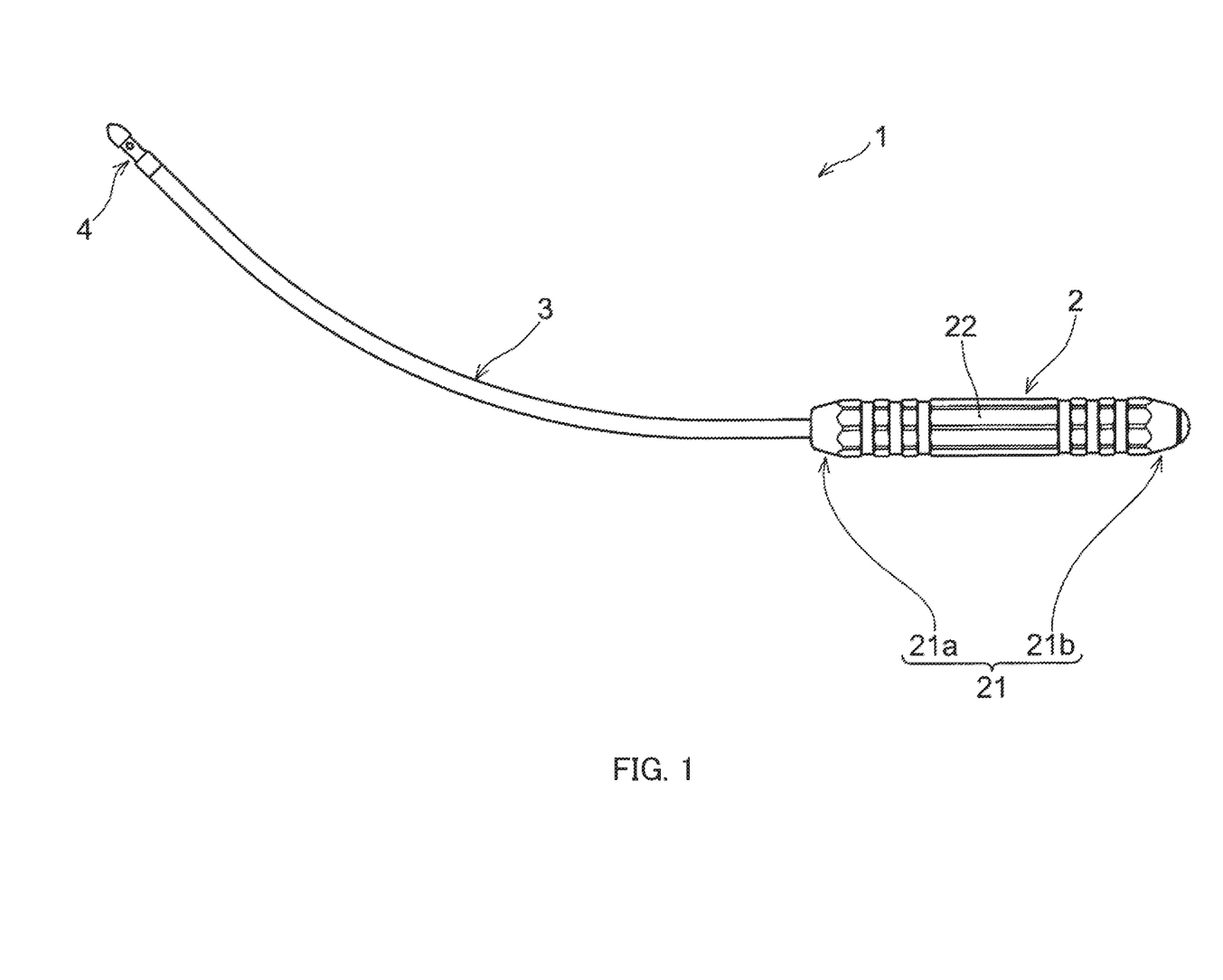
FIG. 1 is an overall view of a tunnel device of one embodiment of the present invention.

As illustrated in FIG. 1, tunnel device 1 of the present embodiment includes base portion 2, shaft 3 connected to base portion 2 at one end of shaft 3, and tip portion 4 connected to the other end of shaft 3.

Tunnel device 1 is used to form a subcutaneous tunnel and to implant an artificial blood vessel in the formed subcutaneous tunnel, and is also called "tunneler" or the like. As a subcutaneous tunnel formation method by tunnel device 1, for example, a subcutaneous tunnel is formed by inserting tunnel device 1 between a first incision part (not illustrated) formed on a skin, such as an arm, and provided for subcutaneously introducing tunnel device 1, and a second incision part (not illustrated) for leading out tip portion 4 of tunnel device 1 to the outside of the body. After a subcutaneous tunnel is formed, an artificial blood vessel is connected to tip portion 4 of tunnel device 1, then pulled into the subcutaneous tunnel, and sutured with an existing blood vessel, and thus the artificial blood vessel is implanted. Note that, applications of tunnel device 1 are not limited to the implanting of an artificial blood vessel described above.

Base portion 2 is a portion which supports tunnel device 1, and is a part serving as a handle at the time of formation of a subcutaneous tunnel by tunnel device 1. Shaft 3 is detachably connected to base portion 2. Base portion 2 is used in the state of being in connection with shaft 3 and serves as an operation portion when shaft 3 and tip portion 4 are conducted subcutaneously. Base portion 2 is capable of providing a force applied to base portion 2 at the time of formation of a subcutaneous tunnel by tunnel device 1 to shaft 3 and is also capable of supporting a force applied in a radial direction and an axial direction of shaft 3. In this embodiment, base portion 2 is formed in a substantially columnar shape having a larger cross section than a cross section perpendicular to the axial direction of shaft 3 in a cross section perpendicular to the axial direction of shaft 3 connected to base portion 2. Base portion 2 is formed in a holdable shape with size.

As illustrated in FIG. 1, base portion 2 is provided with shaft connection portion 21 to which one end of shaft 4 is connected. In the present embodiment, shaft connection portion 21 is provided on a side of one end of base portion 2, and the one end of shaft 3 is connected. In the present embodiment, as illustrated in FIG. 1 to FIG. 3, base portion 2 includes first shaft connection portion 21a and second shaft connection portion 21b on both ends of base portion 2, but it is sufficient as long as shaft connection portion 21 is provided in at least one of the end portions of base portion 2.

Figure 2:
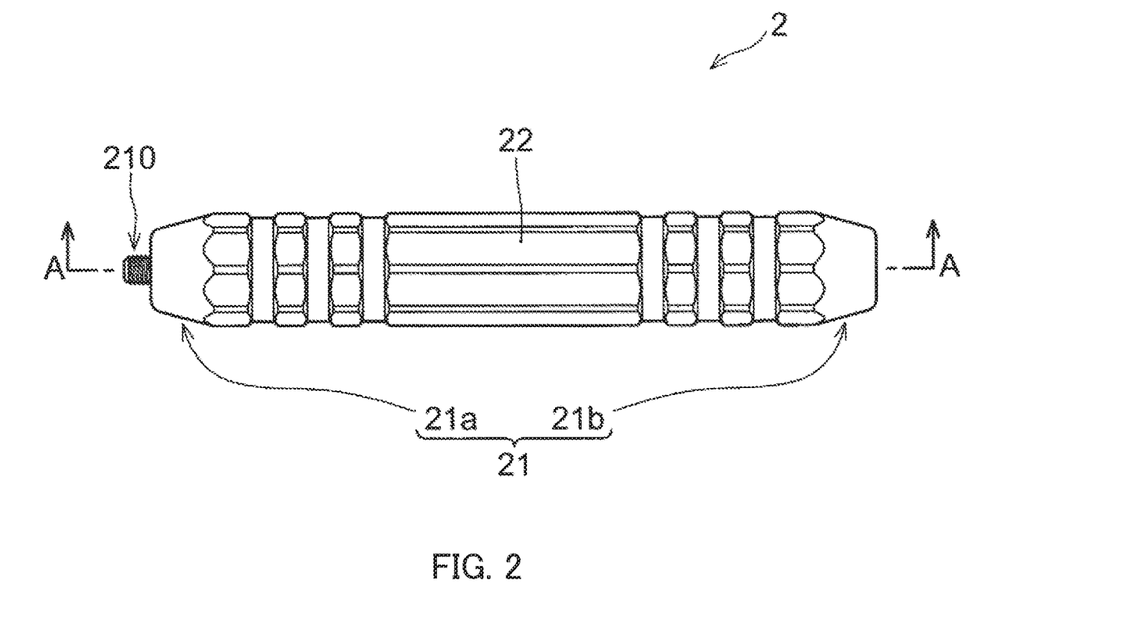
FIG. 2 is a diagram illustrating a base portion of the tunnel device of FIG. 1.
Figure 3:
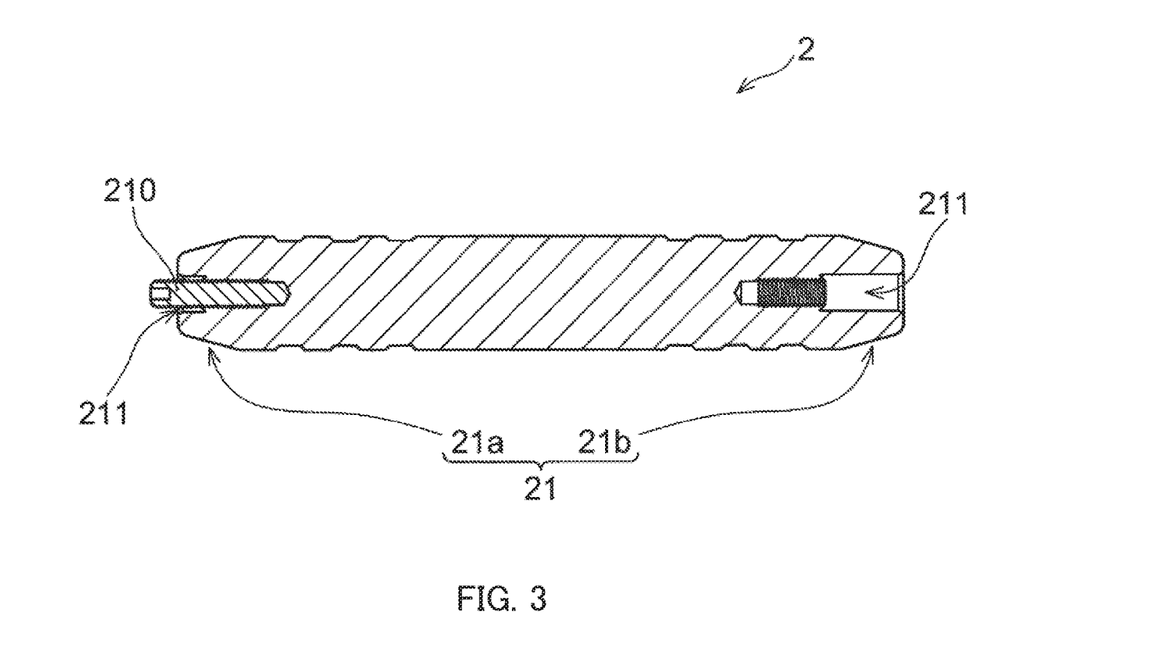
FIG. 3 is a cross-sectional view taken along A-A line of FIG. 2.

In the present embodiment, base portion 2 includes handle portion 22 to be held at the time of formation of a subcutaneous tunnel by tunnel device 1, and shaft connection portion 21 is provided on a side of one end of handle portion 22 (on sides of both ends in FIG. 2). Handle portion 22 is a part to be held by an operator, such as a doctor. Handle portion 22 is provided with recession and protrusion which functions as a slip resistance, but as long as handle portion 22 can be held in a way that allows a force to be transmitted to shaft 3 at the time of formation of a subcutaneous tunnel by tunnel device 1, the shape and/or structure of handle portion 22 is not particularly limited.

Shaft connection portion 21 connects shaft 3 and base portion 2 with each other and transmits an operational force applied to base portion 2 to shaft 3. In the present embodiment, shaft connection portion 21 includes base-portion-side screw portion 210 (see FIG. 2 and FIG. 3) as will be described later and base-portion-side screw portion 210 is screwed with shaft-side screw portion 31 (see FIG. 4) provided in one end of shaft 3 and connects base portion 2 to shaft 3.

Shaft 3 is formed so as to be capable of forming a subcutaneous tunnel into which an artificial blood vessel is insertable. As long as shaft 3 has a configuration that makes it possible to form a subcutaneous tunnel having a length and/or a hole diameter which is set in accordance with the purpose, it is sufficient as shaft 3. The cross-sectional shape of shaft 3 is not particularly limited, but it is preferable that shaft 3 have a shape that allows shaft 3 to be smoothly inserted when shaft 3 is conducted subcutaneously, such as a substantially circular shape of a cross section perpendicular to a length direction of shaft 3, for example. Shaft 3 can have a body portion capable of forming a subcutaneous tunnel having a desired shape. Further, the material of shaft 3 is not particularly limited as long as the material is biocompatible and has a rigidity that allows a subcutaneous tunnel to be formed. As the material of shaft 3, for example, a stainless material can be used.

Figure 4:
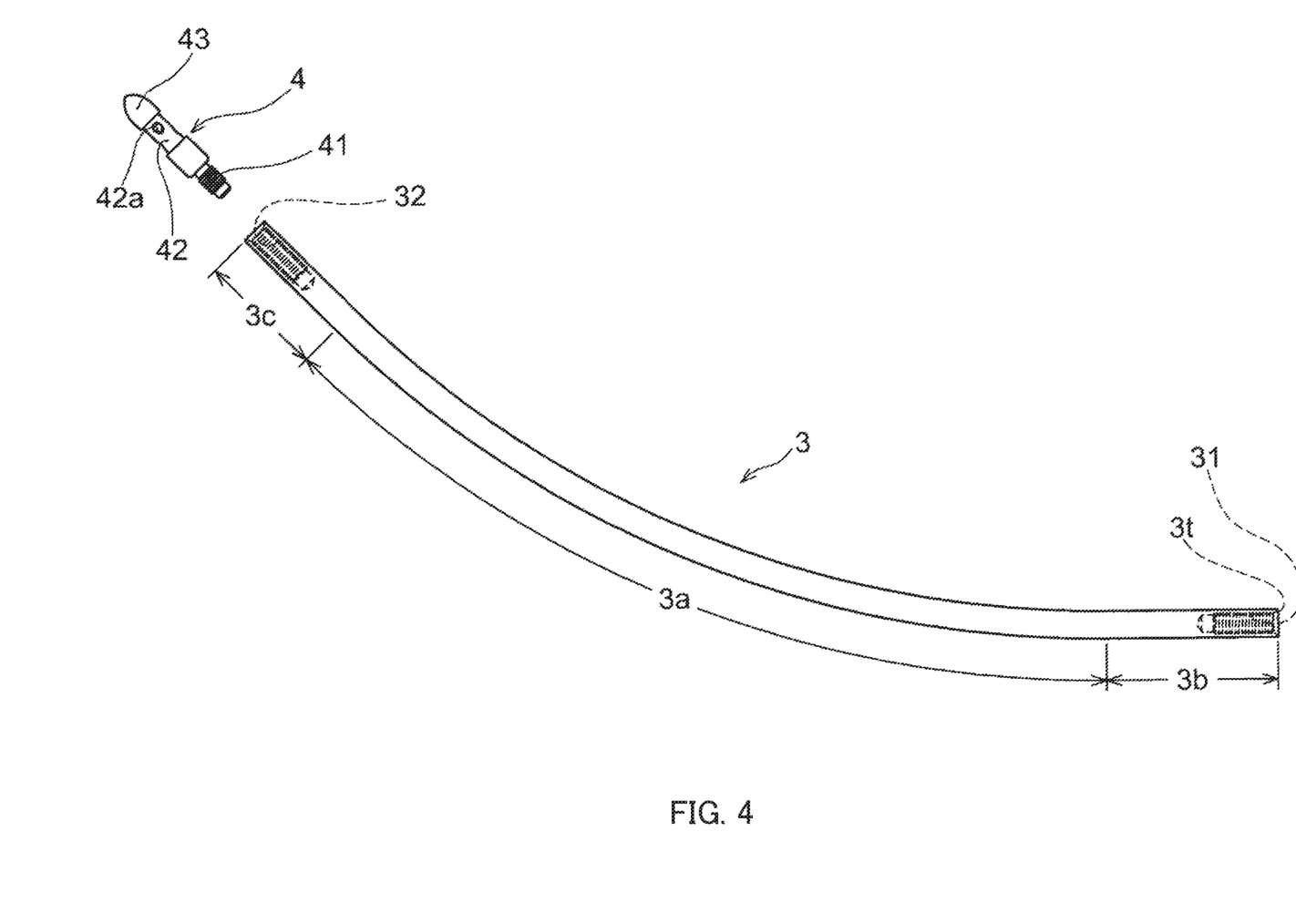
FIG. 4 is a diagram illustrating a shaft and a tip portion of the tunnel device in FIG. 1.

Shaft 3 is connected to base portion 2 at one of end portions of shaft 3 and is connected to tip portion 4 at the other end portion. In the present embodiment, both ends of shaft 3 are screwed and connected to base portion 2 and tip portion 4. As illustrated in FIG. 4, one end of shaft 3 is provided with shaft-side screw portion 31 to be screwed with base-portion-side screw portion 210 provided in the base portion. Shaft 3 and base portion 2 are connected to each other by screwing shaft-side screw portion 31 with base-portion-side screw portion 210 (see FIG. 5). As illustrated in FIG. 4, in the present embodiment, second shaft-side screw portion 32 is provided in the other end of shaft 3. Second shaft-side screw portion 32 is screwed with tip-portion-side screw portion 41 of tip portion 4, and thus, tip portion 4 and shaft 3 are connected with each other. Note that, the same structure as that of shaft-side screw portion 31 (first shaft-side screw portion) provided in the one end of shaft 3 can be adopted for second shaft-side screw portion 32.

In the present embodiment, shaft 3 includes curved portion 3a, first connection portion 3b provided in an end portion of one side of curved portion 3a, and second connection portion 3c provided in an end portion of the other side of curved portion 3a, as illustrated in FIG. 4. Curved portion 3a is a part curved along the length direction of shaft 3. The curve shape of curved portion 3a of shaft 3 is not limited to the illustrated curve shape. Curved portion 3a of shaft 3 may have a different curve shape and/or curvature so as to allow a subcutaneous tunnel to be formed into a desired path.

First connection portion 3b and second connection portion 3c are provided so as to be connectable to shaft connection portion 21. As illustrated in FIG. 4, first connection portion 3b occupies a predetermined region from a side of one end of shaft 3 in the length direction of shaft 3. Second connection portion 3c occupies a predetermined region from a side of the other end of shaft 3 in the length direction of shaft 3. In the present embodiment, first connection portion 3b and second connection portion 3c have shaft-side screw portion 31 and second shaft-side screw portion 32, respectively. Shaft-side screw portion 31 and second shaft-side screw portion 32 can be screwed with base-portion-side screw portion 210 of base portion 2 and tip-portion-side screw portion 41 of tip portion 4, respectively. First connection portion 3b and second connection portion 3c can be set to a separate state from a connection state from base portion 2 and tip portion 4, respectively. Note that, the combination of first connection portion 3b and second connection portion 3c to which base portion 2 and tip portion 4 are to be connected may be switched and connected in accordance with the shape of a subcutaneous tunnel to be formed and/or an operation method.

In the present embodiment, shaft-side screw portion 31 and second shaft-side screw portion 32 are each formed as a female screw portion provided on an inner peripheral surface of a recess portion formed in the end portion and extending in the axial direction, but they may each be a male screw portion protruding from an end portion of shaft 3, for example.

Tip portion 4 is located in a top portion of tunnel device 1 at the time of formation of a subcutaneous tunnel and forms a subcutaneous tunnel with shaft 3. The shape and structure of tip portion 4 may be one that causes tip portion 4 to tear tissue and move forward subcutaneously, and in the present embodiment, tip portion 4 has a protruding shape which protrudes sharply. In the present embodiment, tip portion 4 includes tip-portion-side screw portion 41 which connects between tip portion 4 and shaft 3, joint portion 42 for attaching an artificial blood vessel to tunnel device 1 by a suture thread and/or the like, and boring portion 43 having a tapered bullet-shaped head, as illustrated in FIG. 4. In the present embodiment, joint portion 42 is provided between tip-portion-side screw portion 41 and boring portion 43. Joint portion 42 includes insertion hole 42a which is capable of covering one end of an artificial blood vessel and through which a suture thread is inserted for fixing the covered artificial blood vessel to tip portion 4 by the suture thread. Although tip-portion-side screw portion 41 is illustrated as a male screw portion in the present embodiment, in a case where shaft-side screw portion 31 and second shaft-side screw portion 32 are each formed of a male screw portion, for example, they can be female screw portions. Moreover, the joint portion need not be necessarily provided in tip portion 4, and the joint portion may be provided in an end portion of shaft 3.

In order to form a subcutaneous tunnel, tunnel device 1 in which base portion 2, shaft 3, and tip portion 4 are connected with each other is pushed in, for example, from the first incision part, and moves forward subcutaneously. When tip portion 4 having entered from the first incision part reaches the second incision part and exits to the outside of the body, an artificial blood vessel is attached to tip portion 4. When an artificial blood vessel is attached to tip portion 4, tunnel device 1 is operated such that shaft 3 is pulled out from the subcutaneous tunnel. Then, a predetermined operation is performed, and the artificial blood vessel is sutured with an existing blood vessel, and an operation is completed. Note that, the use method by tunnel device 1 described above is just an example, and the use method of tunnel device 1 is not particularly limited.

Figure 5:
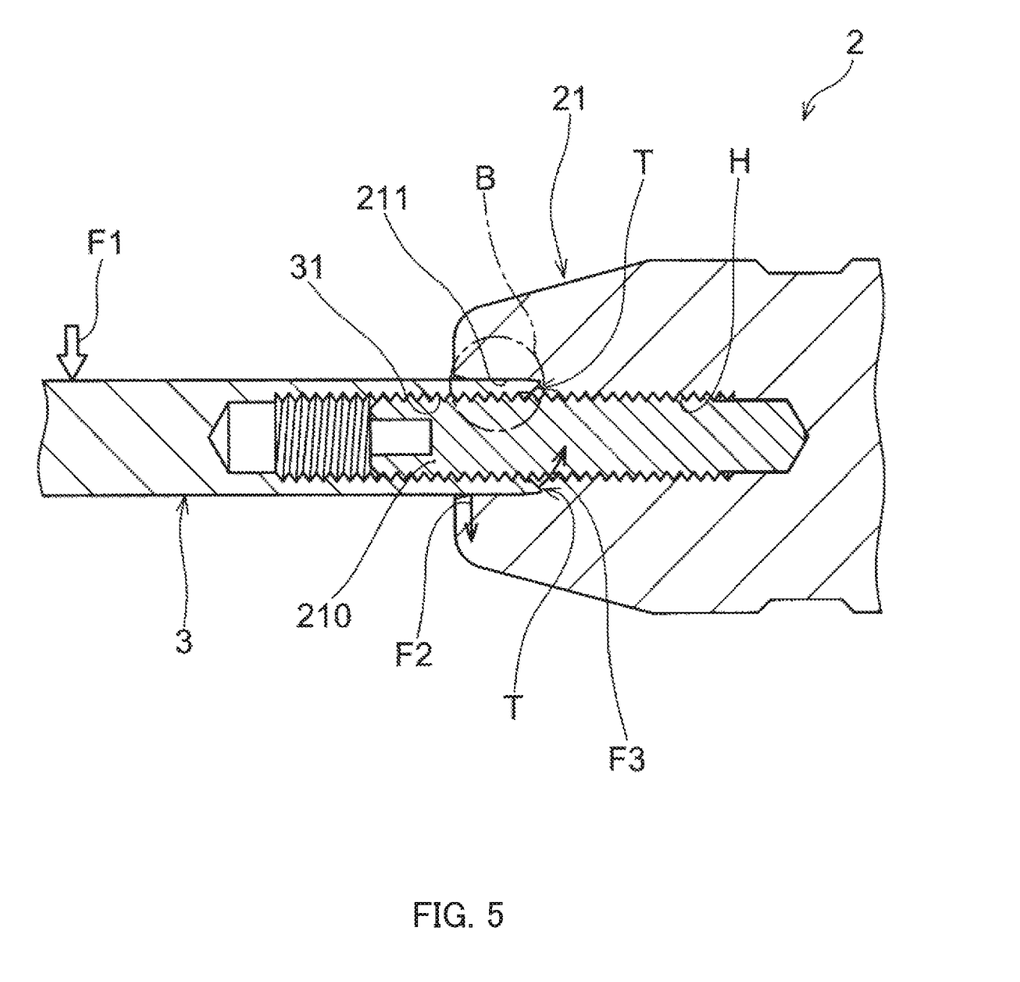
FIG. 5 is a cross-sectional view of a connection part between the base portion and the shaft of the tunnel device, which is obtained by cutting along an axial direction of the base portion.

In the present embodiment, as illustrated in FIG. 5, shaft connection portion 21 includes shaft housing portion 211 having an inner diameter substantially same as an outer diameter of one end of shaft 3, and base-portion-side screw portion 210 provided on a further inner side relative to shaft housing portion 211. Base portion 2 and shaft 3 are fixed to each other by screwing between shaft-side screw portion 31 and base-portion-side screw portion 210.

Shaft housing portion 211 houses one end of shaft 3. In the present embodiment, as illustrated in FIG. 5, shaft housing portion 211 is a recess portion provided with a predetermined length along the axial direction of base portion 2 from an end portion of base portion 2. Shaft housing portion 211 is formed such that an inner peripheral surface of shaft housing portion 211 comes into contact with an outer peripheral surface of one end of shaft 3. In the present embodiment, shaft housing portion 211 has an inner diameter substantially same as an outer diameter of one end of shaft 3 and is formed such that the inner peripheral surface of shaft housing portion 211 faces the outer peripheral surface of one end of shaft 3 substantially with no gap. In this embodiment, the outer peripheral surface of shaft 3 is a cylindrical surface, and shaft housing portion 211 is formed as a space of a substantially columnar shape corresponding to the shape of the outer peripheral surface of shaft 3. Note that, in this embodiment, no screw portion is formed on the inner peripheral surface of shaft housing portion 211. Shaft housing portion 211 has a length in the axial direction allowing one end of shaft 3 to be housed therein and suppressing arrival of a body fluid or cell to shaft-side screw portion 31 from an opening which is the tip of shaft housing portion 211. Even when a body fluid or cell enters from an opening into which one end of shaft 3 is inserted in a state where shaft 3 is housed in shaft housing portion 211, there is almost no gap between shaft 3 and shaft housing portion 211, and thus, further entry to a depth side of shaft housing portion 211 is suppressed. For this reason, deposition of a component of a body fluid and/or cell is suppressed in shaft-side screw portion 31 and/or base-portion-side screw portion 210, and thus, tunnel device 1 is readily washable and is hygienic.

In the present embodiment, the inner peripheral surface of an opening end portion which forms the opening in base portion 2 is formed in a tapered shape in which the inner peripheral surface of the opening end portion widens radially toward a side of opening edge E (see FIG. 6) of shaft housing portion 211, which becomes an entry side where shaft 3 is to be inserted. Since shaft housing portion 211 is formed in the tapered shape on a side of opening edge E, the outer periphery of shaft 3 is not readily damaged when shaft 3 is bent.

Figure 6:
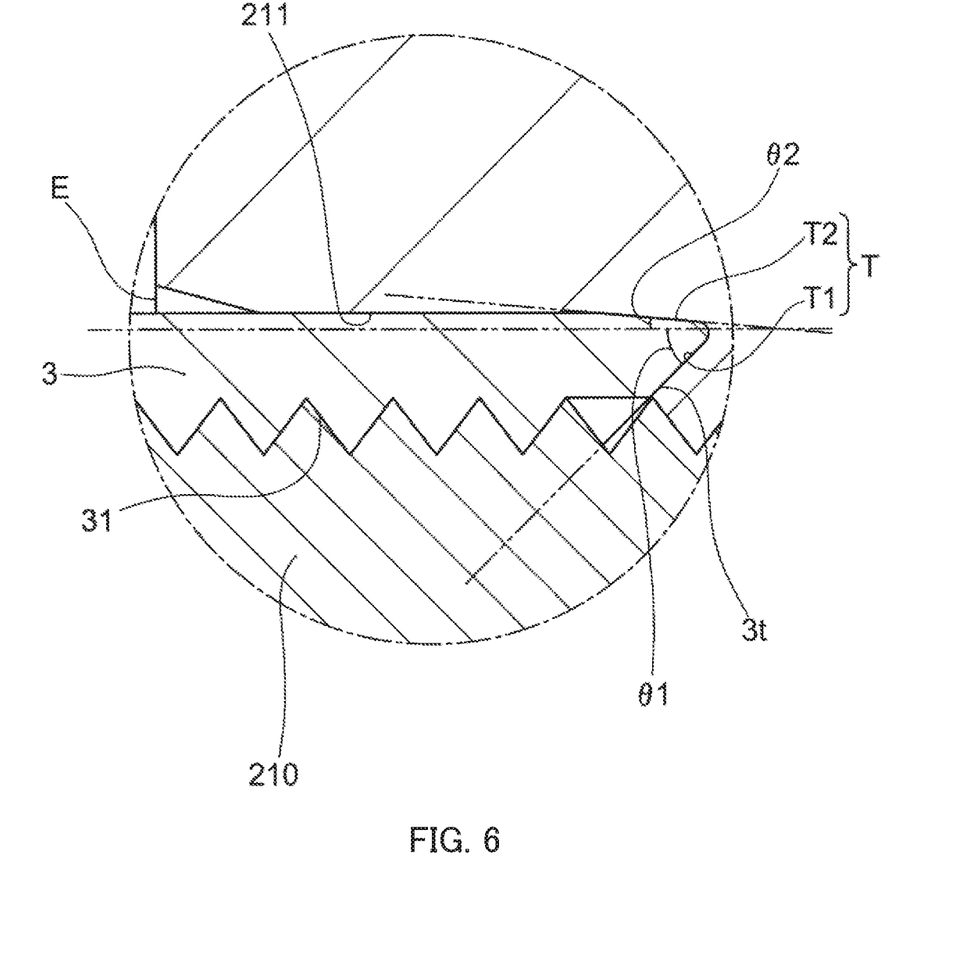
FIG. 6 is a partially enlarged view of region B of FIG. 5.

As illustrated in FIG. 5 and an FIG. 6, base-portion-side screw portion 210 is formed to be screwed with shaft-side screw portion 31 of shaft 3, and shaft 3 and base portion 2 are detachable. As illustrated in FIG. 5 and FIG. 6, base-portion-side screw portion 210 is provided on a radially inner side relative to the inner peripheral surface of shaft housing portion 211 on one end of shaft 3 to be inserted. Base-portion-side screw portion 210 is formed as a screw structure in which a jig for rotation is insertable in one of end portions, and for example, can be a setscrew.

The shape and structure of base-portion-side screw portion 210 allows for screwing with shaft-side screw portion 31 and can be provided on a further radially inner side relative to shaft housing portion 211. It is preferable that base-portion-side screw portion 210 be provided coaxially with shaft housing portion 211. Base-portion-side screw portion 210 may be a male screw or a female screw. In the present embodiment, as illustrated in FIG. 5, base-portion-side screw portion 210 has a male screw portion formed to be screwed with shaft-side screw portion 31 having a female screw portion on the inner peripheral surface of one end of shaft 3 formed in a cylindrical shape. In the present embodiment, base-portion-side screw portion 210 extends on a radially inner side of the inner peripheral surface of shaft housing portion 211. Although base-portion-side screw portion 210 is illustrated as an attachment screw attachable and detachable with respect to base portion 2 in the present embodiment, base-portion-side screw portion 210 may be formed integrally with base portion 2. Note that, in the present embodiment, as illustrated in FIG. 5, base-portion-side screw portion 210 illustrated as an attachment screw is attached to screw hole H which has an inner diameter smaller than the inner peripheral surface of shaft housing portion 211 and which axially continues to shaft housing portion 211.

Note that, in a case where shaft-side screw portion 31 is formed as a male screw, for example, base-portion-side screw portion 210 may be formed as a female screw which is provided coaxially with shaft housing portion 211 and continuously with shaft housing portion 211 in axial direction, and which is formed on an inner peripheral surface of recess portion having a smaller inner diameter than shaft housing portion 211 (e.g., screw hole H or the like). In this case, for example, shaft-side screw portion 31 is formed such that a male screw which is one size smaller than an outer diameter of shaft 3 protrudes axially from one end of shaft 3.

In this embodiment, as described above, shaft connection portion 21 of base portion 2 includes shaft housing portion 211 having an inner diameter substantially same as an outer diameter of one end of shaft 3, and base-portion-side screw portion 210 provided on a further inner side relative to shaft housing portion 211. Accordingly, the outer peripheral surface of shaft 3 and the inner peripheral surface of shaft housing portion 211 face each other so as to be capable of coming into contact with each other in a radially outer side position relative to a position where base-portion-side screw portion 210 and shaft-side screw portion 31 are screwed with each other. For this reason, in a case where a force is applied to shaft 3, such as a case where shaft 3 is conducted subcutaneously, for example, the outer peripheral surface of one end of shaft 3 housed in shaft housing portion 211 comes into contact with the inner peripheral surface of shaft housing portion 211. One end of shaft 3 is pressed by the inner peripheral surface of shaft housing portion 211 from an outer peripheral side. Accordingly, tilting of one end of shaft 3 in shaft housing portion 211 is suppressed, and no gap is readily generated in the joint position between shaft 3 and base portion 2, or widening of a gap is suppressed. For this reason, entry of a body fluid and/or the like, such as blood, into shaft housing portion 211 and/or the screwed portion between base-portion-side screw portion 210 and shaft-side screw portion 31 is suppressed, and thus, hygienic safety is provided. In particular, when a body fluid and/or the like enters a screw portion, the cleaning operation becomes hard. In the present embodiment, generation of a gap and/or widening of a gap between the inner peripheral surface of shaft housing portion 211 and the outer peripheral surface of shaft 3, which is a radially outer side relative to the screwed portion between base-portion-side screw portion 210 and shaft-side screw portion 31, is suppressed. Accordingly, in the entry path for a body fluid and/or the like, a gap where a body fluid and/or the like enters is suppressed in a position before the screwed portion between base-portion-side screw portion 210 and shaft-side screw portion 31. Thus, it is hard for the body fluid to arrive at the screwed portion, and thus, contamination in the screwed portion where a cleaning operation is hard can be further prevented.

Moreover, in the present embodiment, as illustrated in FIG. 5 and FIG. 6, base portion 2 includes base-portion-side tapered portion T provided in shaft housing portion 211. Moreover, shaft-side tapered portion 3t which is connectable in a tapered manner with base-portion-side tapered portion T is provided in one end of shaft 3.

Base-portion-side tapered portion T is connected in a tapered manner (hereinafter, referred to as "taper-connected") with shaft-side tapered portion 3t. Base-portion-side tapered portion T has a taper surface (first tapered portion T1 to be described later) which is taper-connected with shaft-side tapered portion 3t, and the taper surface of base-portion-side tapered portion T is inclined with respect to the axial direction of base portion 2. In the present embodiment, base-portion-side tapered portion T is a depth-side wall portion of shaft housing portion 211 in the insertion direction of shaft 3. In the present embodiment, the taper surface of base-portion-side tapered portion T is inclined so as to widen radially outward as proceeding forward to a depth side (right side in FIG. 5) in the insertion direction of shaft 3 into shaft housing portion 211. Note that, the taper surface of base-portion-side tapered portion T may be inclined so as to narrow radially inward as proceeding forward in a direction opposite to the inclination direction illustrated in FIG. 5, that is, as proceeding forward to a depth side in the insertion direction.

Shaft-side tapered portion 3t is taper-connected with base-portion-side tapered portion T. As illustrated in FIG. 6, shaft-side tapered portion 3t has a taper surface inclined with respect to the axial direction of one end of shaft 3. Shaft-side tapered portion 3t is formed such that shaft-side tapered portion 3t is inclined in a direction substantially same as the inclination direction of base-portion-side tapered portion T and a taper surface of base-portion-side tapered portion T and a taper surface of shaft-side tapered portion 3t face each other.

Figure 7:
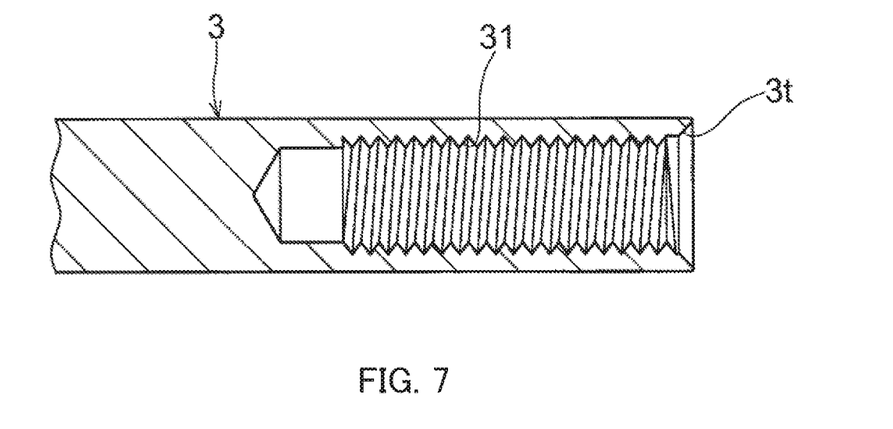
FIG. 7 is a cross-sectional view obtained by cutting one end of the shaft of the tunnel device of FIG. 1 in the axial direction.

Shaft-side tapered portion 3t is taper-connected with base-portion-side tapered portion T when shaft 3 is screwed with base portion 2. In the present embodiment, shaft-side tapered portion 3t is provided in an end portion of shaft 3 as illustrated in FIG. 6 and FIG. 7. Shaft-side tapered portion 3t is inclined such that an inclined surface of shaft-side tapered portion 3t widens radially outward to the tip of shaft 3. Note that, as long as shaft-side tapered portion 3t is taper-connected with base-portion-side tapered portion T and includes a taper surface in accordance with the inclination of base-portion-side tapered portion T, it is sufficient as shaft-side tapered portion 3t.

Note that, shaft-side tapered portion 3t need not be an end edge of one end of shaft 3, and as long as shaft-side tapered portion 3t is connectable in a tapered manner with base-portion-side tapered portion T when shaft 3 is housed in shaft housing portion 211, shaft-side tapered portion 3t may have a protruding portion, such as a male screw portion, on a further tip side in the axial direction relative to shaft-side tapered portion 3t.

In the present embodiment, when shaft 3 is screwed with base portion 2, base-portion-side tapered portion T and shaft-side tapered portion 3t are taper-connected with each other. Thus, base-portion-side tapered portion T and shaft-side tapered portion 3t come into contact with each surface. In this state, when a force as indicated by arrow F1 in FIG. 5 is applied to shaft 3, for example, shaft 3 attempts to tilt with respect to base portion 2 such that the left side of shaft 3 is lowered in FIG. 5. In this case, although various forces act, for example, for the force applied to base portion 2 from shaft 3 indicated by arrow F2 of FIG. 5, the inner peripheral surface of shaft housing portion 211 holds the outer peripheral surface of shaft 3 from radially outward. Moreover, for the force applied from shaft 3 indicated by arrow F3 in the tip of shaft 3 by the force indicated by arrow F1, force F3 is supported from radially inward by the surface contact due to the tapered connection between base-portion-side tapered portion T and shaft-side tapered portion 3t. While shaft 3 is held from radially outward by the inner peripheral surface of shaft housing portion 211, shaft 3 is held from radially inward by connecting base-portion-side tapered portion T and shaft-side tapered portion 3t with each other in a tapered manner. Thus, holding shaft 3 from both radially outward and radially inward suppresses tilting of shaft 3 in shaft housing portion 211, and thus, formation of a gap between shaft 3 and shaft housing portion 211 is suppressed. Accordingly, entry of a body fluid and/or the like into the screwed portion between base-portion-side screw portion 210 and shaft-side screw portion 31 is further suppressed. Furthermore, loosening of the screwed part of shaft 3 with respect to base portion 2 is suppressed by the tapered connection between base-portion-side tapered portion T and shaft-side tapered portion 3t. Accordingly, backlash and/or the like due to loosening of shaft-side screw portion 31 with respect to base-portion-side screw portion 210 is eliminated, and generation and/or widening of a gap is further suppressed, and suppression effects for entry of a body fluid and/or the like can be enhanced.

Moreover, in the present embodiment, as illustrated in FIG. 6, base-portion-side tapered portion T includes first tapered portion T1 and second tapered portion T2 which are inclined in the axial direction of base portion 2. First tapered portion T1 and second tapered portion T2 are provided so as to intersect with each other in the axial direction and provided such that taper angle θ1 of first tapered portion T1 with respect to the axial direction is larger than taper angle θ2 of second tapered portion T2 with respect to the axial direction.

First tapered portion T1 is a tapered portion to be taper-connected to shaft-side tapered portion 3*t*, as described above. Second tapered portion T2 is a tapered portion inclined in a reverse direction so as to face first tapered portion T1 in a radial direction. In the present embodiment, as illustrated in FIG. 6, first tapered portion T1 is inclined radially outward as proceeding forward in the insertion direction of shaft 3, and second tapered portion T2 is inclined radially inward as proceeding forward in the insertion direction of shaft 3. Second tapered portion T2 comes into contact with the outer peripheral surface of one end of shaft 3 and is formed so as to be taper-connected with the outer peripheral surface of one end of shaft 3. The one end of shaft 3 is taper-connected from the outer peripheral side and the inner peripheral side of shaft 3 by first tapered portion T1 and second tapered portion T2.

In the present embodiment, because of the presence of second tapered portion T2, even when the outer peripheral surface of one end of shaft 3 attempts to widen radially outward by the taper connection between first tapered portion T1 and shaft-side tapered portion 3*t*, second tapered portion T2 comes into contact with the outer peripheral surface of shaft 3. Thus, while the function to prevent loosening of the screwed portion between shaft 3 and base portion 2 by the tapered connection between first tapered portion T1 and shaft-side tapered portion 3*t* is maintained, widening of the outer peripheral surface of one end of shaft 3 radially outward resulting in deformation is suppressed. For this reason, widening of the outer peripheral surface of one end of shaft 3 resulting in deformation, which makes insertion of shaft 3 into shaft housing portion 211 harder, is prevented, and insertion readiness of shaft 3 into shaft housing portion 211 is enhanced. Furthermore, widening of the outer peripheral surface of one end of shaft 3, which makes pulling out of shaft 3 from shaft housing portion 211 harder, is prevented, and thus, reduction in pullability of shaft 3 can be prevented. Note that, as long as reduction in the insertion readiness and pullability of shaft 3 into and from shaft housing portion 211 can be suppressed, and the function to prevent loosening of the screwed portion can be maintained, the angles of first tapered portion T1 and second tapered portion T2 with respect to the axial direction are not particularly limited. Furthermore, second tapered portion T2 need not be entirely provided circumferentially in the inner peripheral surface of shaft housing portion 211, and as long as second tapered portion T2 is partly provided circumferentially in the inner peripheral surface, it is sufficient as second tapered portion T2. In the present embodiment, base-portion-side tapered portion T is provided so as to face the outer peripheral side of base portion 2, but base-portion-side tapered portion T may be inclined so as to face a center axis of base portion 2.

In the present embodiment, as described above, first connection portion 3*b* and second connection portion 3*c* of shaft 3 are provided so as to be connectable to shaft connection portion 21. First connection portion 3*b* of shaft 3 is connectable to both shaft connection portion 21 of base portion 2 and tip portion 4. Moreover, second connection portion 3*c* of shaft 3 is connectable to both shaft connection portion 21 of base portion 2 and tip portion 4. When first connection portion 3*b* is connected to shaft connection portion 21 of base portion 2, second connection portion 3*c* is connected to tip portion 4. Further, when first connection portion 3*b* is connected to tip portion 4, second connection portion 3*c* is connected to shaft connection portion 21 of base portion 2. In the present embodiment, first connection portion 3*b* and second connection portion 3*c* have shaft-side screw portion 31 and second shaft-side screw portion 32, respectively. Shaft-side screw portion 31 and second shaft-side screw portion 32 are formed so as to be capable of being screwed with base-portion-side screw portion 210 and tip-portion-side screw portion 41, respectively.

Figure 8:
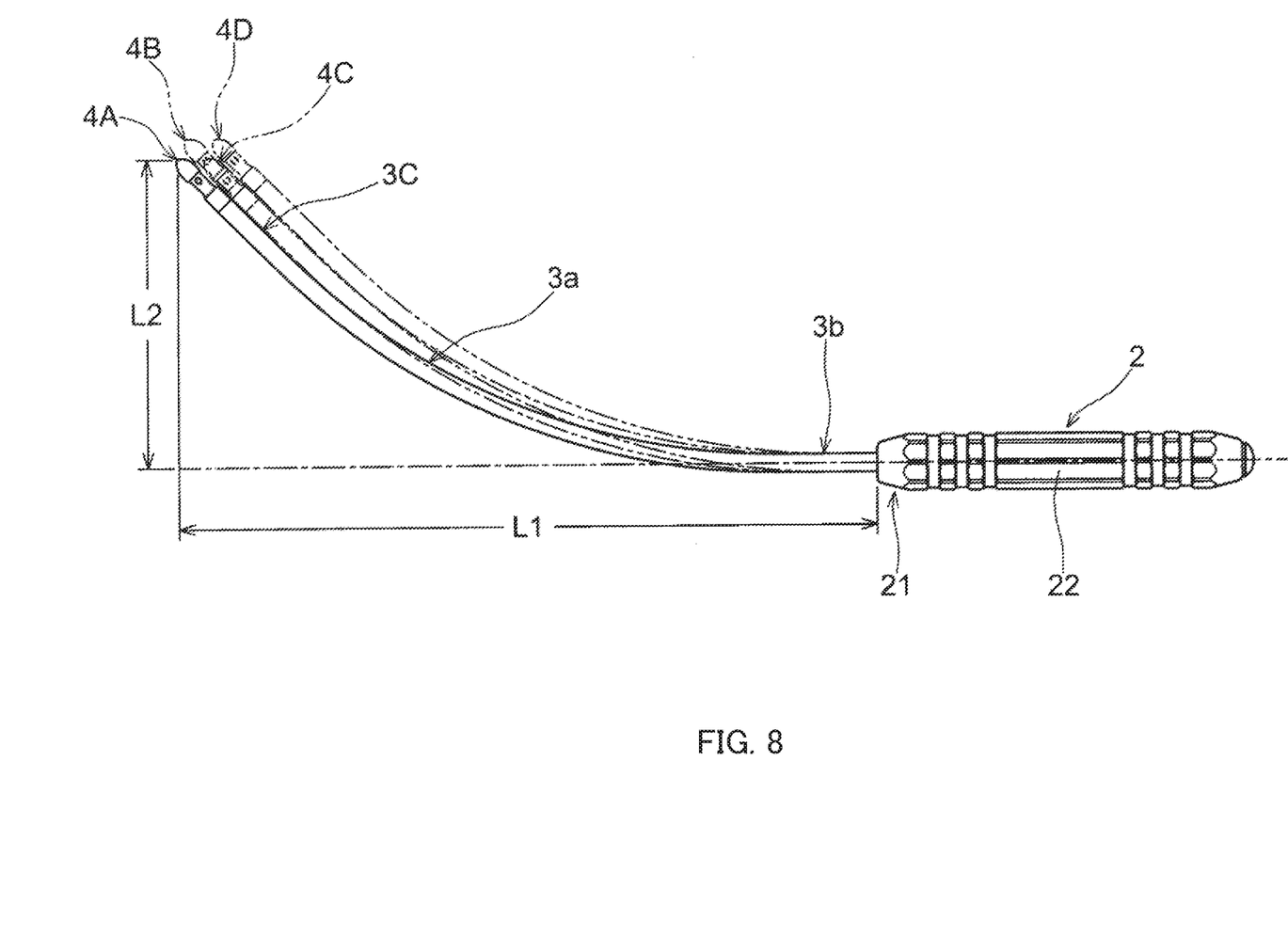
FIG. 8 is a diagram illustrating a state where a relative position of the tip portion of the tunnel device of FIG. 1 has changed.

In the present embodiment, as illustrated in FIG. 8, first connection portion 3*b* is configured, with respect to second connection portion 3*c*, such that a relative position of tip portion 4 with respect to base portion 2 in a state where first connection portion 3*b* is connected to shaft connection portion 21 is different from a relative position of tip portion 4 with respect to base portion 2 in a state where second connection portion 3*c* is connected to shaft connection portion 21. As described above, in this embodiment, the relative position of tip portion 4 with respect to base portion 2 can be varied, for example, as illustrated in FIG. 8, from the position denoted by reference numeral 4A to the position denoted by reference numeral 4B, between a case where first connection portion 3*b* on a side of one end of shaft 3 is connected to shaft connection portion 21 and a case where second connection portion 3*c* on a side of the other end of shaft 3 is connected to shaft connection portion 21. Note that, as to the relative position of tip portion 4 with respect to base portion 2, for example, as long as any one of a length from the end portion of base portion 2 to which shaft 3 is connected to the tip of tip portion 4 in the axial direction of base portion 2 (base-portion-side screw portion 210) (L1 in FIG. 8) and a distance from the axis of base portion 2 (base-portion-side screw portion 210) to the tip of tip portion 4 (L2 in FIG. 8) is different, it is sufficient as the configuration.

As described above, in a case where the relative position of tip portion 4 is varied by first connection portion 3*b* and second connection portion 3*c*, as illustrated in FIG. 8, the position of tip portion 4 with respect to base portion 2 can be adjusted. For this reason, in accordance with the body shape of a patient and/or the relative position between the first incision part and the second incision part respectively serving as an inlet and an outlet of tunnel device 1, the distance between base portion 2 and tip portion 4 can be changed. Accordingly, at least two different shaft shapes with which the relative positions of tip portion 4 are different can be achieved with single tunnel device 1. Furthermore, in this embodiment, not only the distance between base portion 2 and tip portion 4, but also the distance between curved portion 3*a* and base portion 4, and the distance between curved portion 3*a* and tip portion 4, and angles can be changed.

In a case where the relative position of tip portion 4 is varied by first connection portion 3*b* and second connection portion 3*c*, the following configuration is sufficient in which a side including first connection portion 3*b* and a side including second connection portion 3c are asymmetric from the center portion of a length direction of shaft 3, for example. In this embodiment, as illustrated in FIG. 4, first connection portion 3b and second connection portion 3c are formed so as to extend substantially linearly, and by changing the lengths of first connection portion 3b and second connection portion 3c (first connection portion 3b is longer than second connection portion 3c), as illustrated in FIG. 8, when shaft 3 is connected to base portion 2, the position of the point of origin of curved portion 3a with respect to base portion 2 (boundary between curved portion 3a and first connection portion 3b or second connection portion 3c) changes. For this reason, the position where shaft 3 starts curving changes between a case where first connection portion 3b is connected to base portion 2 and a case where second connection portion 3c is connected to base portion 2. Accordingly, the relative position of tip portion 4 with respect to base portion 2 can be varied. Note that, first connection portion 3b and second connection portion 3c need not be necessarily linear, and for example, first connection portion 3b and second connection portion 3c may include a curved portion. In this case, the relative position of tip portion 4 can be changed by changing the curvatures of the curved portions of first connection portion 3b and second connection portion 3c to be different from each other.

Further, in this embodiment, base portion 2 includes first shaft connection portion 21a and second shaft connection portion 21b on both ends of base portion 2, as illustrated in FIG. 3. Second shaft connection portion 21b is formed such that an end portion of shaft 3 is inserted into second shaft connection portion 21b deeper than into first shaft connection portion 21a and connected thereto. In this case, the position of tip portion 4 changes between the case where shaft 3 is connected to first shaft connection portion 21a and the case where shaft 3 is connected to second shaft connection portion 21b as indicated by reference numerals 4A and 4C in FIG. 8. In this embodiment, the state indicated by reference numeral 4A is a state where first connection portion 3b is connected to first shaft connection portion 21a. Further, the state indicated by reference numeral 4C is a state where first connection portion 3b is connected to second shaft connection portion 21b. In FIG. 8, the position of tip portion 4 indicated by reference numeral 4C has shifted to the side of base portion 2 relative to the position of tip portion 4 indicated by reference numeral 4A by the amount of the portion of first connection portion 3b which has been inserted into second shaft connection portion 21b deeper than into first shaft connection portion 21a. Note that, in FIG. 8, the state indicated by reference numeral 4B is the state where second connection portion 3c is connected to first shaft connection portion 21a, and the state indicated by reference numeral 4D is the state where second connection portion 3c is connected to second shaft connection portion 21b. In this case as well, the position of tip portion 4 indicated by reference numeral 4D has shifted to the side of base portion 2 relative to the position of tip portion 4 indicated by reference numeral 4B by the amount of the portion of second connection portion 3c which has been inserted into second shaft connection portion 21b deeper than into first shaft connection portion 21a.

REFERENCE SIGNS LIST

1 Tunnel device
2 Base portion
21 Shaft connection portion
21a First shaft connection portion
21b Second shaft connection portion
210 Base-portion-side screw portion
211 Shaft housing portion
22 Holding portion
3 Shaft
31 Shaft-side screw portion
32 Second shaft-side screw portion
3a Curved portion
3b First connection portion
3c Second connection portion
3t Shaft-side tapered portion
4 Tip portion
41 Tip-portion-side screw portion
42 Joint portion
42a Insertion hole
43 Boring portion
E Opening edge of shaft housing portion
F1, F2, and F3 Force
H Screw hole
L1 Length to tip of tip portion in axial direction of base portion
L2 Distance from axis of base portion to tip of tip portion
T Base-portion-side tapered portion
T1 First tapered portion
T2 Second tapered portion
$\theta1, \theta2$ Taper angle

What is claimed is:
1. A tunnel device, comprising:
a base portion;
a shaft connected to the base portion at one end of the shaft, the one end of the shaft being a cylindrically shaped end; and
a tip portion connected to another end of the shaft, wherein
the base portion is provided with a shaft connection portion to which the cylindrically shaped end of the shaft is connected,
the shaft is provided with a shaft-side screw portion having a female screw portion on an inner peripheral surface of the cylindrically shaped end of the shaft,
the shaft connection portion includes:
    a shaft housing portion having an inner diameter substantially same as an outer diameter of the cylindrically shaped end of the shaft; and
    a base-portion-side screw portion having a male screw portion provided on a further inner side relative to the shaft housing portion,
the base portion and the shaft are fixed to each other by screwing between the shaft-side screw portion and the base-portion-side screw portion,
the tunnel device further comprises:
    a base-portion-side tapered portion provided in a depth-side wall portion of the shaft housing portion in an insertion direction of the shaft; and
    a shaft-side tapered portion provided in an end edge of the cylindrically shaped end of the shaft such that the shaft-side tapered portion is connected in a tapered manner with and has surface contact with the base-portion-side tapered portion when the base portion and the shaft are fixed to each other,
the base-portion-side tapered portion includes a first tapered portion and a second tapered portion which are inclined in an axial direction of the base portion,
the first tapered portion and the second tapered portion are provided so as to intersect with each other in the axial direction, and the first tapered portion and the second tapered portion are provided such that a taper angle of the first tapered portion with respect to the axial direction is greater than a taper angle of the second tapered portion with respect to the axial direction.

2. The tunnel device according to claim 1, wherein the shaft includes:

a curved portion;

a first connection portion provided in an end portion of one side of the curved portion; and a second connection portion provided in an end portion of another side of the curved portion, wherein the first connection portion and the second connection portion are provided so as to be connectable to the shaft connection portion, and the first connection portion is formed, with respect to the second connection portion, such that a relative position of the tip portion with respect to the base portion in a state where the first connection portion is connected to the shall connection portion and a relative position of the tip portion with respect to the base portion in a state where the second connection portion is connected to the shall connection portion are different from each other.

3. A tunnel device, comprising:

a base portion;

a shaft connected to the base portion at one end of the shaft; and a tip portion connected to another end of the shaft, wherein the base portion is provided with a shaft connection portion to which the one end of the shaft is connected, the shaft is provided with a shaft-side screw portion at the one end of the shaft, the shaft connection portion includes:

a shaft housing portion having an inner diameter substantially same as an outer diameter of the one end of the shaft; and a base-portion-side screw portion provided on a further inner side relative to the shaft housing portion, the base portion and the shaft are fixed to each other by screwing between the shaft-side screw portion and the base-portion-side screw portion, the tunnel device further comprises:

a base-portion-side tapered portion provided in the shaft housing portion; and a shaft-side tapered portion connectable in a tapered manner with the base-portion-side tapered portion, the shaft-side tapered portion being provided in the one end of the shaft, the base-portion-side tapered portion includes a first tapered portion and a second tapered portion which are inclined in an axial direction of the base portion, the first tapered portion and the second tapered portion are provided so as to intersect with each other in the axial direction, and the first tapered portion and the second tapered portion are provided such that a taper angle of the first tapered portion with respect to the axial direction is greater than a taper angle of the second tapered portion with respect to the axial direction.

\* \* \* \* \*